US011638688B2

(12) United States Patent
Constantine et al.

(10) Patent No.: US 11,638,688 B2
(45) Date of Patent: May 2, 2023

(54) COMPOSITION

(71) Applicant: COSMETIC WARRIORS LIMITED, Poole (GB)

(72) Inventors: Mark Constantine, Poole (GB); Margaret Joan Constantine, Poole (GB); Helen Elizabeth Ambrosen, Wimborne (GB); Rowena Jacqueline Bird, Christchurch (GB)

(73) Assignee: COSMETIC WARRIORS LIMITED, Poole (GB)

( * ) Notice: Subject to any disclaimer, the term of this patent is extended or adjusted under 35 U.S.C. 154(b) by 1114 days.

(21) Appl. No.: 15/568,443

(22) PCT Filed: Apr. 21, 2016

(86) PCT No.: PCT/GB2016/051105
§ 371 (c)(1),
(2) Date: Oct. 20, 2017

(87) PCT Pub. No.: WO2016/170339
PCT Pub. Date: Oct. 27, 2016

(65) Prior Publication Data
US 2018/0153793 A1 Jun. 7, 2018

(30) Foreign Application Priority Data
Apr. 22, 2015 (GB) .................................. 1506825

(51) Int. Cl.
*A61K 8/92* (2006.01)
*A61K 8/73* (2006.01)
*A61Q 19/00* (2006.01)

(52) U.S. Cl.
CPC .............. *A61K 8/922* (2013.01); *A61K 8/732* (2013.01); *A61Q 19/007* (2013.01); *A61K 2800/30* (2013.01); *A61K 2800/5922* (2013.01)

(58) Field of Classification Search
None
See application file for complete search history.

(56) References Cited

U.S. PATENT DOCUMENTS

| 4,659,562 | A | * | 4/1987 | Arraudeau | A61Q 1/06 424/63 |
| 5,229,130 | A | * | 7/1993 | Sharma | A61K 9/0014 424/448 |
| 6,004,584 | A | * | 12/1999 | Peterson | A61K 8/25 424/489 |
| 8,063,005 | B2 | * | 11/2011 | Kalidindi | A61K 8/9794 510/139 |
| 2003/0077962 | A1 | * | 4/2003 | Krzysik | A61K 8/0208 442/100 |
| 2003/0082219 | A1 | * | 5/2003 | Warren | A61F 13/51305 424/401 |
| 2003/0133900 | A1 | | 7/2003 | McLaughlin | |
| 2008/0299103 | A1 | | 12/2008 | George et al. | |
| 2009/0130220 | A1 | | 5/2009 | Johnson | |
| 2013/0287708 | A1 | | 10/2013 | Silberstein et al. | |

FOREIGN PATENT DOCUMENTS

| JP | S60-25907 | A | 2/1985 |
| JP | S63-135326 | A | 6/1988 |
| JP | 2003-531846 | A | 10/2003 |
| JP | 2008-156286 | A | 7/2008 |
| JP | 2013-525342 | A | 6/2013 |
| JP | 2014-031337 | A | 2/2014 |
| KR | 20100053083 | A | 5/2010 |
| RU | 2242216 | C1 | 12/2004 |
| WO | 01/37792 | A2 | 5/2001 |
| WO | 01/082889 | A1 | 11/2001 |
| WO | 2005/035013 | A1 | 4/2005 |
| WO | 2008/079898 | A1 | 7/2008 |
| WO | 2011/132177 | A1 | 10/2011 |
| WO | 2012/077120 | A2 | 6/2012 |
| WO | 2014/091196 | A2 | 6/2014 |

OTHER PUBLICATIONS 2019, https://helenatur.com/en/vegetable-butters/.*
2019, https://www.turkchem.net/starch-as-a-multi-functional-additive-in-cosmetics.html.*
2017, https://aromaticingredients.com.au/blogs/news/which-vegetable-oil-will-benefit-your-formulation-part-2.*
Office Action for Russian Patent Application No. 2017140469/04(070290), dated Jun. 19, 2019.
International Search Report and Written Opinion for PCT/GB2016/051105, dated Jun. 24, 2016.
Search Report for British Patent Application No. 1506825.7, dated Jan. 21, 2016.
A. Truman, "DIY Homemade Lotion—3 Receipes for Textures", brokeandhealthy.com [online], Available from: http://web.archive.org/web/20131003114439/http://www.brokeandhealthy.com/diy-homemade-lotion-3-recipes-for-3-textures [Accessed Jan. 18, 2016].
Search Report for Japanese Patent Application No. 2017-553072, dated Jan. 24, 2020, 12 pages.
Office Action for Japanese Patent Application No. 2017-553072, dated Jan. 31, 2020, 8 pages.
Office Action for Great Britain Patent Application No. 1506825.7, dated Jan. 14, 2020, 4 pages.
Office Action for Russian Patent Application No. 2017140469, dated Mar. 19, 2020.

* cited by examiner

*Primary Examiner* — Terry A McKelvey
*Assistant Examiner* — Catheryne Chen
(74) *Attorney, Agent, or Firm* — Merchant & Gould P.C.

(57) ABSTRACT

A cosmetic composition includes: (i) one or more vegetable butters in an amount of from 5 to 35% by weight of the total composition; (ii) one or more vegetable oils in an amount of from 20 to 50% by weight of the total composition; and (iii) starch in an amount of from 40 to 85% by weight of the total composition. The cosmetic composition is free from preservatives as defined herein.

16 Claims, No Drawings

COMPOSITION

This application is a National Stage of PCT/GB2016/051105, filed 21 Apr. 2016, which claims benefit of British Patent Application No. 1506825.7, filed 22 Apr. 2015 which applications are incorporated herein by reference. To the extent appropriate, a claim of priority is made to each of the above disclosed applications.

FIELD OF THE INVENTION

The present invention relates to a product for use as a cosmetic, a process for producing said product, and a product prepared by the method.

BACKGROUND TO THE INVENTION

The present invention relates to products particularly those for use in contact with the human body. The present invention relates to the increasing demand for fresh and natural cosmetics.

The rise of natural cosmetics to the pinnacle of the modern beauty industry is not a recent phenomenon. Humans have been using moisturisers since the Mesolithic era (10,000 years ago). The Sumerians combined wine, tree oils and plant, animal or mineral materials before applying to the body. The ancient Egyptian civilisation is known to have used olive oil, sesame oil, myrrh resin as well as bitter almonds, honey and cardamom to care for the skin. But it was the celebrated Roman physician Galen who created cold cream in 200 BC, by melting beeswax into rose oil then adding water.

After centuries of homemade remedies, the use of cosmetics became wide spread in the 1800's. The rise in popular new materials like Petroleum Jelly, Mineral Oil and Lanolin allowed the development of new cosmetics and high sales volumes. These new ingredients were far less expensive than beeswax and rose oil. Products such as Hinds Honey & Almond Cream formulated in 1872 by a Pharmacist from Maine in the U.S. enabled the use of cosmetics by many more people, particularly women anxious to keep their skin soft and healthy. However it was the advent of television and the rise in advertising that led to the initial boom in the 1930's.

Modern cosmetic products are formulated to have a very long shelf life. The shelf life of a typical product is thirty one months. However, before products reach a retail environment, they are shipped and then stored in warehouses, sometimes for years before sale. Products may be labelled with a 'best used by date' but without an indication of when they were made. Consequently many formulations are assembled with longevity more in mind than effect.

Consumers are increasingly concerned with the ingredients used in their cosmetics. There have been numerous reports in the media linking various materials in cosmetics with increased risk of various diseases including cancer. One materials category that has been associated with these stories on numerous occasions is preservatives.

The purpose of cosmetic preservatives is to prevent the growth of microorganisms (including yeasts & moulds), which would have a detrimental influence on the effect or the appearance of the product as well as being a risk to human health. However substantial use of preservatives can be employed to increase shelf life and therefore the profitability of cosmetics. In response to media or consumer pressure the industry may switch from one preservative system to another, however it would be more desirable to provide a range of effective preservative free cosmetics. By eliminating preservative systems from cosmetics, it would be possible to eliminate worries of consumers, such as bioaccumulation through repetitive use. It would also be possible to reduce the environmental impact of the cosmetic products. The use of preservatives in the manufacture of products and use by the consumer leads to the contamination of the environment by these materials.

The present invention seeks to provide a cosmetic product which does not contain preservatives at a significant concentration, if at all.

SUMMARY OF THE INVENTION

In a first aspect, there is provided a cosmetic moisturising composition comprising
(i) one or more vegetable butters in an amount of from 5 to 35% by weight of the total composition;
(ii) one or more vegetable oils in an amount of from 20 to 50% by weight of the total composition; and
(iii) starch in an amount of from 40 to 85% by weight of the total composition; wherein the cosmetic moisturising composition is free from preservatives, wherein free from preservatives is as defined herein.

In a second aspect, there is provided a process for the production of a cosmetic moisturising composition as defined herein,
the process comprising the step of mixing:
(i) one or more vegetable butters in an amount of from 5 to 35% by weight of the total composition;
(ii) one or more vegetable oils in an amount of from 20 to 50% by weight of the total composition; and
(iii) starch in an amount of from 40 to 85% by weight of the total composition;
wherein the cosmetic moisturising composition is free from preservatives, wherein free from preservatives is as defined in the description.

In a third aspect, there is provided a product obtained or obtainable by a process as described herein,
wherein the cosmetic moisturising composition is free from preservatives, wherein free from preservatives is as defined in the description.

In a fourth aspect, there is provided a cosmetic method comprising contacting the skin of a user with a cosmetic moisturising composition as defined herein.

The term "free from preservatives" means that the composition contains any of the preservatives listed in Table 1 in amounts of no greater than the amounts specified. Preferably the composition is free from all of the preservatives listed in Table 1.

TABLE 1

| Preservative | Present in an amount no greater than (based on the total composition) |
|---|---|
| Benzoic acid | 0.062% wt. |
| Sodium benzoate | 0.062% wt. |
| Salts of benzoic acid excluding sodium benzoate | 0.003% w/v |

TABLE 1-continued

| Preservative | Present in an amount no greater than (based on the total composition) |
|---|---|
| Propionic acid and salts thereof | 0.0032% w/v |
| Salicylic acid and salts thereof | 1% w/v |
| Hexa-2,4-dienoic acid and salts thereof | 0.4% w/v |
| Formaldehyde | 0.01% w/v |
| Paraformaldehyde | 0.01% w/v |
| Biphenyl-2-ol and salts thereof | $1 \times 10^{-5}$% w/v |
| Pyrithione zinc | $1.6 \times 10^{-4}$% w/v |
| Inorganic sulphites | $1.6 \times 10^{-5}$% w/v |
| Hydrogen sulphites | $1.6 \times 10^{-5}$% w/v |
| Chlorobutanol | 0.25% w/v |
| 4-Hydroxybenzoic acid and salts thereof and esters thereof | $1.2 \times 10^{-2}$% w/v |
| 3-Acetyl-6-methylpyran-2,4(3H)-dione and salts thereof | $1 \times 10^{-3}$% w/v |
| Formic acid | $6 \times 10^{-3}$% w/v |
| Sodium formate | $6 \times 10^{-3}$% w/v |
| Methenamine 3-chloroallylochloride | $5 \times 10^{-3}$% w/v |
| 1-(4-Chlorophenoxy)-1-(imidazole-1-yl)-3,3-dimethylbutan-2-one | $6.3 \times 10^{-5}$% w/v |
| 1,3-Bis (hydroxymethyl)-5,5-dimethylimidazolidine-2,4-dione | $6.3 \times 10^{-5}$% w/v |
| Benzyl alcohol | 0.0625% w/v |
| 1-Hydroxy-4-methyl-6-(2,4,4-trimethylpentyl) 2-pyrindon | $1.6 \times 10^{-5}$% w/v |
| Monoethanolamine salt of 1-Hydroxy-4-methyl-6-(2,4,4-trimethylpentyl) 2-pyrindon | $1.6 \times 10^{-5}$% w/v |
| 2,2'-methylenebis(6-bromo-4-chlorophenol) | $2 \times 10^{-3}$% w/v |
| 4-Isopropyl-m-cresol | 0.1% w/v |
| 5-Chloro-2-methyl-isothiazol-3(2H)-one | $1.6 \times 10^{-3}$% w/v |
| 2-methyl-isothiazol-3(2H)-one | $1.6 \times 10^{-3}$% w/v |
| 2-Benzyl-4-chlorophenol | 0.1% w/v |
| 2-Chloroacetamide | $6.25 \times 10^{-3}$% w/v |
| N,N''-bis(chlorophenyl)-3,12-diamino-2,4,11,13-tetraazatetradecadiamidine | $5 \times 10^{-4}$% w/v |
| digluconate of N,N''-bis(chlorophenyl)-3,12-diamino-2,4,11,13-tetraazatetradecadiamidine | $5 \times 10^{-4}$% w/v |
| diacetate of N,N''-bis(chlorophenyl)-3,12-diamino-2,4,11,13-tetraazatetradecadiamidine | $5 \times 10^{-4}$% w/v |
| dihydrochloride of N,N''-bis(chlorophenyl)-3,12-diamino-2,4,11,13-tetraazatetradecadiamidine | $5 \times 10^{-4}$% w/v |
| 1-Phenoxypropanol-2-ol | 0.1% w/v |
| Alkyl($C_{12-22}$)trimethyl ammonium bromide | $6.1 \times 10^{-3}$% w/v |
| Alkyl($C_{12-22}$)trimethyl ammonium chloride | $6.1 \times 10^{-3}$% w/v |
| 4,4-Dimethyl-1,3-oxazolidine | $3 \times 10^{-6}$% w/v |
| N-(hydroxymethyl)-N-(dihydroxymethyl-1,3-dioxo-2,5-imidazolidinyl-4)-N'(hydroxymethyl) urea | $3 \times 10^{-5}$% w/v |
| Benzenecarboximidamide, 4,4'-(1,6-hexanediylbis (oxy))bis- | 0.116% w/v |
| Salts of Benzenecarboximidamide, 4,4'-(1,6-hexanediylbis (oxy))bis- | 0.116% w/v |
| Glutaraldehyde (pentane-1,5-dial) | $5 \times 10^{-4}$% w/v |
| 5-Ethyl-3,7-dioxa-1-azabicyclo[3.3.0] octane | $1.5 \times 10^{-4}$% w/v |
| 3-(p-Chlorophenoxy)-propane-1,2 diol | 1.25% w/v |
| Sodium hydroxymethylamino acetate | $2 \times 10^{-5}$% w/v |
| Silver chloride | $3.12 \times 10^{-3}$% w/v |
| Benzalkonium chloride | $4 \times 10^{-3}$% w/v |
| Benzalkonium bromide | $4 \times 10^{-3}$% w/v |
| Benzalkonium saccharinate | $4 \times 10^{-3}$% w/v |
| Phenylmethoxy methanol | $3 \times 10^{-5}$% w/v |
| 3-Iodo-2-propynylbutylcarbamate | $6.25 \times 10^{-3}$% w/v |

In the process of the present invention, the process preferably excludes a step of addition one or more prohibited preservatives. The prohibited preservatives are those listed in Table 2.

TABLE 2

| | |
|---|---|
| Benzoic acid | 5-Chloro-2-methyl-isothiazol-3(2H)-one |
| Sodium benzoate | 2-methyl-isothiazol-3(2H)-one |
| Salts of benzoic acid excluding sodium benzoate | 2-Benzyl-4-chlorophenol |

TABLE 2-continued

| | |
|---|---|
| Propionic acid and salts thereof | 2-Chloroacetamide |
| Salicylic acid and salts thereof | N,N''-bis(chlorophenyl)-3,12-diamino-2,4,11,13-tetraazatetradecadiamidine |
| Hexa-2,4-dienoic acid and salts thereof | digluconate of N,N''-bis(chlorophenyl)-3,12-diamino-2,4,11,13-tetraazatetradecadiamidine |
| Formaldehyde | diacetate of N,N''-bis(chlorophenyl)-3,12-diamino-2,4,11,13-tetraazatetradecadiamidine |
| Paraformaldehyde | dihydrochloride of N,N''-bis(chlorophenyl)-3,12-diamino-2,4,11,13-tetraazatetradecadiamidine |
| Biphenyl-2-ol and salts thereof | 1-Phenoxypropanol-2-ol |
| Pyrithione zinc | Alkyl($C_{12-22}$)trimethyl ammonium bromide |
| Inorganic sulphites | Alkyl($C_{12-22}$)trimethyl ammonium chloride |
| Hydrogen sulphites | 4,4-Dimethyl-1,3-oxazolidine |
| Chlorobutanol | N-(hydroxymethyl)-N-(dihydroxymethyl-1,3-dioxo-2,5-imidazolidinyl-4)-N'(hydroxymethyl) urea |
| 4-Hydroxybenzoic acid and salts thereof and esters thereof | Benzenecarboximidamide, 4,4'-(1,6-hexanediylbis (oxy))bis- |
| 3-Acetyl-6-methylpyran-2,4(3H)-dione and salts thereof | Salts of Benzenecarboximidamide, 4,4'-(1,6-hexanediylbis (oxy))bis- |
| Formic acid | Glutaraldehyde (pentane-1,5-dial) |
| Sodium formate | 5-Ethyl-3,7-dioxa-1-azabicyclo[3.3.0] octane |
| Methenamine 3-chloroallylochloride | 3-(p-Chlorophenoxy)-propane-1,2 diol |
| 1-(4-Chlorophenoxy)-1-(imidazole-1-yl)-3,3-dimethylbutan-2-one | Sodium hydroxymethylamino acetate |
| 1,3-Bis (hydroxymethyl)-5,5-dimethylimidazolidine-2,4-dione | Silver chloride |
| Benzyl alcohol | Benzalkonium chloride |
| 1-Hydroxy-4-methyl-6-(2,4,4-trimethylpentyl) 2-pyrindon | Benzalkonium bromide |
| Monoethanolamine salt of 1-Hydroxy-4-methyl-6-(2,4,4-trimethylpentyl) 2-pyrindon | Benzalkonium saccharinate |
| 2,2'-methylenebis(6-bromo-4-chlorophenol) | Phenylmethoxy methanol |
| 4-Isopropyl-m-cresol | 3-Iodo-2-propynylbutylcarbamate |

The present invention relates to a range of cosmetic products that are free of preservatives, yet are still resistant to microbial growth. Preferably the cosmetic moisturising composition of the present invention is used as a skin moisturiser. The cosmetic moisturising compositions of the present invention provide the user with a desirable product that is capable of being stored at room temperature and that may have a shelf life of from six weeks to twenty months. Typically the product will be packaged in a pot or bottle with a label noting when the product was made and advising when it should be used by.

An advantage of the present invention is that a blend of vegetable butters and vegetable oils can be specifically formulated depending on skin type and condition. For example:

Grapeseed oil contains high levels of linoleic acid, which helps maintain the skin's barrier function and acts as an anti-inflammatory. This is especially beneficial for delicate skin.

Olive oil is rich in α-tocopherol, squalene, phenols and phytosterols, which help prevent ageing of the skin due to their antioxidant and UV absorption properties.

Jojoba oil is miscible with the skin's sebum, and therefore provides exceptional transepidermal respiration and moisture control, resulting in a highly emolliating, non-greasy oil that does not block the skin's pores. This is particularly beneficial for individuals with psoriasis, dermatitis and acne.

Cocoa butter contains a wide variety of fatty acids, which enable it to improve skin moisture retention and elasticity. It also contains cocoa mass polyphenol, which is known to suppress the production of immunoglobulin IgE. IgE is understood to aggravate the symptoms of dermatitis and rashes.

Shea butter is a highly effective emollient and moisturising vegetable butter. It contains large amounts of vitamins A and E, which help to strengthen and repair the skin, in addition to caffeic acid and cinnamic acid, which help reduce inflammation and swelling. Furthermore shea butter is non-comedogenic, which makes it particularly useful for sensitive areas around the face and neck.

A disadvantage of using these butters and oils is that they produce a shiny or tacky feeling to the user, which is both aesthetically undesirable and physiologically detrimental as dirt and oils can become trapped, resulting in an undesirable effect on the skin.

We found that, by using a specific balance of starch, vegetable butter and vegetable oil, the excess oil and dirt was absorbed and removed from the skin allowing the penetration of the desired oils and butters into the skin, thereby allowing them to produce the desired effects.

A further advantage of using a starch in combination with the vegetable butter and vegetable composition was that the desired composition did not separate and a light cream or balm could be formed. This meant that additional water was not required to lighten the composition, thereby removing the requirement for preservatives. It was found that the systems set out in the present invention had an exceptional shelf life and substantially resisted microbial growth, including yeasts and moulds.

Therefore, in some embodiments, the composition of the present invention is free or substantially free of water. As used herein, the term "free or substantially free of water" means that the composition comprises water in an amount of less than 5% by weight of the total composition, such as less than 1% by weight of the total composition, such as less 0.5% by weight of the total composition, such as less than 0.25% by weight of the total composition, such as less than 0.1% by weight of the total composition, such as less than 0.01% by weight of the total composition, such as less than 0.001% by weight of the total composition.

In one aspect of the present invention, there is provided a cosmetic moisturising composition comprising
(i) one or more vegetable butters in an amount of from 5 to 35% by weight of the total composition;
(ii) one or more vegetable oils in an amount of from 20 to 50% by weight of the total composition; and
(iii) starch in an amount of from 40 to 85% by weight of the total composition; wherein the cosmetic moisturising composition is free from preservatives, wherein free from preservatives is as defined herein,
and wherein the cosmetic moisturising composition comprises essentially no water.

The composition of the present invention is free from preservatives and is able to deliver exceptional moisturising, emolliating and remedial properties, without the undesirable qualities that are often associated with the direct application of vegetable oils and vegetable butters.

For ease of reference, these and further aspects of the present invention are now discussed under appropriate section headings. However, the teachings under each section are not necessarily limited to each particular section.

DETAILED DESCRIPTION

Composition

As discussed herein, in one aspect of the present invention, there is provided a cosmetic moisturising composition comprising
(i) one or more vegetable butters in an amount of from 5 to 35% by weight of the total composition;
(ii) one or more vegetable oils in an amount of from 20 to 50% by weight of the total composition; and
(iii) starch in an amount of from 40 to 85% by weight of the total composition; wherein the cosmetic moisturising composition is free from preservatives, wherein free from preservatives is as defined herein.

The cosmetic moisturising composition may contain one or more additional components such as to provide the desired cosmetic composition.

In one aspect the cosmetic moisturising composition is a liquid composition. In one aspect the cosmetic moisturising composition is a solid composition. Solid products of the present invention are compositions which can substantially sustain their physical shape when unsupported by external means, e.g. packaging etc. Thus, they are considered to be solid, solid-like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid. The solid form of the solid compositions of the present invention mean that external packaging is not required to maintain the shape of the composition.

Vegetable Butter

As discussed herein, in one aspect of the present invention, there is provided a cosmetic moisturising composition comprising
(i) one or more vegetable butters in an amount of from 5 to 35% by weight of the total composition;
(ii) one or more vegetable oils in an amount of from 20 to 50% by weight of the total composition; and
(iii) starch in an amount of from 40 to 85% by weight of the total composition;
wherein the cosmetic moisturising composition is free from preservatives, wherein free from preservatives is as defined herein.

In various aspects of the present invention the one or more vegetable butters is present in an amount of
from 5 to 35% by weight of the total composition;
from 5 to 30% by weight of the total composition;
from 10 to 30% by weight of the total composition;
from 10 to 25% by weight of the total composition;
from 15 to 25% by weight of the total composition;
from 15 to 20% by weight of the total composition.

The term vegetable butter is understood by one skilled in the art and means a triglyceride obtainable from a vegetable source which has the consistency of butter.

The vegetable butters used in the present invention are triglycerides which are found to be solid (including solid-like, discussed above) at normal usage temperatures. For the avoidance of doubt the vegetable butter is a triglyceride which remains substantially solid at up to 30° C. It will be appreciated however that it is not a requirement that the vegetable butter have a solid fat content of 100% at normal usage temperatures. In a preferred aspect the solid fat has a solid fat content of at least 70%, preferably at least 80%, preferably at least 90%, preferably at least 95%, preferably at least 98%, preferably at least 99% at 25° C.

In one aspect the vegetable butter is one or more hard vegetable butters. In one aspect, the vegetable butter is one or more soft vegetable butters. In one aspect, the vegetable butter is a mixture of one or more hard vegetable butters and one or more soft vegetable butters. In one aspect, the vegetable butter is a mixture of a hard vegetable butter and a soft vegetable butter.

The term hard vegetable butter is understood by one skilled in the art and means a high saturated vegetable butter selected from vegetable butters having greater than 60 wt. % saturated fatty acids based on the total fatty acids of the high saturated vegetable butter. The term soft vegetable butter is understood by one skilled in the art and means a low saturated vegetable butter selected from vegetable butters having less than 60 wt. % saturated fatty acids based on the total fatty acids of the low saturated vegetable butter.

The one or more hard vegetable butters (also known as and referred to as high saturated vegetable butters) is preferably selected from Cocoa butter, Illipe butter, Murumuru butter, Kokum butter and mixtures thereof. In a preferred aspect, the one or more hard vegetable butters is Cocoa butter.

The one or more soft vegetable butters (also known as and referred to as low saturated vegetable butters is preferably selected from Aloe butter, Avocado butter, Cupuacu butter, Macadamia Nut butter, Mango butter, Olive butter, Shea butter, Coconut butter, Pumpkin Seed butter, Peanut butter, Almond butter, Coffee Bean butter, Refined butter, Hemp Seed butter, Mochacchino butter, Pistachio Nut butter, Shealoe butter and mixtures thereof. In a preferred aspect, the one or more soft vegetable butters is Shea butter.

In one aspect the one or more vegetable butters is preferably selected from Cocoa butter, Illipe butter, Murumuru butter, Kokum butter, Aloe butter, Avocado butter, Cupuacu butter, Macadamia Nut butter, Mango butter, Olive butter, Shea butter, Coconut butter, Pumpkin Seed butter, Peanut butter, Almond butter, Coffee Bean butter, Refined butter, Hemp Seed butter, Mochacchino butter, Pistachio Nut butter, Shealoe butter and mixtures thereof.

In one aspect the one or more vegetable butter is Cocoa butter. In one aspect the one or more vegetable butters is Shea butter. In one aspect the one or more vegetable butters is a mixture of Cocoa butter and Shea butter.

Preferably the hard vegetable butter and soft vegetable butter are present in a weight ratio of from 95:5 to 5:95, preferably in a weight ratio of from 85:15 to 15:85, preferably in a weight ratio of from 75:25 to 25:75, preferably in a weight ratio of from 65:35 to 35:65, preferably in a weight ratio of from 55:45 to 45:55, preferably in a weight ratio of from 75:25 to 65:35.

Preferably the hard vegetable butter and soft vegetable butter are present in a weight ratio of from 95:5 to 65:35, preferably in a weight ratio of from 85:15 to 75:25. As will be understood by those skilled in the art, the greater the proportion of hard vegetable butter present in the composition the drier it will feel. Drier feeling mixtures of butters are better for areas of the body that are prone to increased perspiration, such as feet and hands. Compositions with increased soft butters feel lighter on the skin, but may produce an increasingly greasy feeling.

Vegetable Oil

As discussed herein, in one aspect of the present invention, there is provided a cosmetic moisturising composition comprising (i) one or more vegetable butters in an amount of from 5 to 35% by weight of the total composition;

(ii) one or more vegetable oils in an amount of from 20 to 50% by weight of the total composition; and (iii) starch in an amount of from 40 to 85% by weight of the total composition; wherein the cosmetic moisturising composition is free from preservatives, wherein free from preservatives is as defined herein.

In various aspects of the present invention the one or more vegetable oils is present in an amount of from 20 to 50% by weight of the total composition;
from 20 to 45% by weight of the total composition;
from 20 to 40% by weight of the total composition;
from 25 to 40% by weight of the total composition;
from 25 to 35% by weight of the total composition;
from 25 to 30% by weight of the total composition.

Preferably the one or more vegetable oils is selected from seasame oil, rosehip oil, almond oil, raspberry seed oil, jojoba oil, avocado oil, castor oil, moringa oil, olive oil, grapeseed oil, argan oil, baobab oil, kalahari melon oil, brazil nut oil and mixtures thereof.

Starch

As discussed herein, in one aspect of the present invention, there is provided a cosmetic moisturising composition comprising (i) one or more vegetable butters in an amount of from 5 to 35% by weight of the total composition;

(ii) one or more vegetable oils in an amount of from 20 to 50% by weight of the total composition; and (iii) starch in an amount of from 40 to 85% by weight of the total composition; wherein the cosmetic moisturising composition is free from preservatives, wherein free from preservatives is as defined herein.

In various aspects of the present invention the starch is present in an amount of from 40 to 85% by weight of the total composition;
from 45 to 85% by weight of the total composition;
from 45 to 80% by weight of the total composition;
from 45 to 75% by weight of the total composition;
from 45 to 70% by weight of the total composition;
from 45 to 65% by weight of the total composition;
from 45 to 60% by weight of the total composition;
from 45 to 55% by weight of the total composition.
from 50 to 60% by weight of the total composition.

Preferably the starch is selected from corn starch, tapioca starch, potato starch and mixtures thereof. In one aspect the starch is corn starch. In one preferred aspect the starch is not rice starch. Therefore, in some embodiments, the composition of the present invention is free or substantially free of rice starch. As used herein, the term "free or substantially free of rice starch" means that the composition comprises rice starch in an amount of less than 5% by weight of the total composition, such as less than 1% by weight of the total composition, such as less than 0.5% by weight of the total composition, such as less than 0.25% by weight of the total composition, such as less than 0.1% by weight of the total composition, such as less than 0.01% by weight of the total composition, such as less than 0.001% by weight of the total composition.

Vegetable Butter, Vegetable Oil & Starch

In one aspect of the present invention, there is provided a cosmetic moisturising composition comprising (i) one or more vegetable butters in an amount of from 5 to 35% by weight of the total composition;

(ii) one or more vegetable oils in an amount of from 20 to 50% by weight of the total composition; and (iii) starch in an amount of from 40 to 85% by weight of the total composition; wherein the cosmetic moisturising composition is free from preservatives, wherein free from preservatives is as defined herein.

In a preferred aspect, there is provided a cosmetic moisturising composition comprising (i) one or more vegetable butters in an amount of from 10 to 30% by weight of the total composition;

(ii) one or more vegetable oils in an amount of from 20 to 40% by weight of the total composition; and (iii) starch in an amount of from 40 to 80% by weight of the total composition; wherein the cosmetic moisturising composition is free from preservatives, wherein free from preservatives is as defined herein.

In a preferred aspect, there is provided a cosmetic moisturising composition comprising (i) one or more vegetable butters in an amount of from 15 to 25% by weight of the total composition;

(ii) one or more vegetable oils in an amount of from 25 to 35% by weight of the total composition; and (iii) starch in an amount of from 40 to 70% by weight of the total composition; wherein the cosmetic moisturising composition is free from preservatives, wherein free from preservatives is as defined herein.

Preferably the one or more vegetable butters and the one or more vegetable oils are present in a weight ratio of from 2:1 to 1:10, preferably in a weight ratio of from 2:1 to 1:5, preferably in a weight ratio of from 1.5:1 to 1:4, preferably in a weight ratio of from 1:1 to 1:3, preferably in a weight ratio of from 1:1 to 1:2.

Further Components

The cosmetic moisturising composition of the present invention may also comprise one or more cosmetically acceptable additives. The skilled person in the art is aware of a range of cosmetically acceptable additives which are suitable for incorporation into such compositions. For example, binders, fillers, opacifiers, perfumes, fragrances, decorative items and mixtures thereof. Preferably, the cosmetic moisturising composition of the present invention further comprises at least one additional component selected from perfumes, colours, fragrances and mixtures thereof.

In a preferred aspect there is provided a cosmetic moisturising composition comprising (i) one or more vegetable butters in an amount of from 5 to 35% by weight of the total composition;

(ii) one or more vegetable oils in an amount of from 20 to 50% by weight of the total composition;

(iii) starch in an amount of from 40 to 85% by weight of the total composition; wherein the cosmetic moisturising composition is free from preservatives, wherein free from preservatives is as defined herein; and (iv) optionally an additional component selected from binders, fillers, opacifiers, perfumes, colours, fragrances and mixtures thereof.

Fragrance may be added to the product to make the experience of using the present composition more pleasant. Combining essential oils such as lavender, chamomile or rose absolute into fragrances for the invention ensures the user has a pleasant moisturising experience.

The amount of fragrances is preferably from about 0.1% to about 10% by weight of the total composition, such as from about 0.1% to about 5% by weight of the total composition, such as from about 0.1% to about 4% by weight of the total composition, such as from about 0.5% to about 5% by weight of the total composition, such as from about 1% to about 5% by weight of the total composition, such as from about 0.5% to about 4% by weight of the total composition, such as from about 0.5% to about 3% by weight of the total composition, such as from about 0.5% to about 2% by weight of the total composition, such as from about 0.5% to about 1.5% by weight of the total composition.

The essential oils may be selected based on the fragrance desired, skin type to be treated and other effects desired based on the well-known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the product are selected from Tarragon, Lemon myrtle, Jasmin, Ylang ylang, Labdanum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, *Litsea Cubeba*, Cardamon, Tonka, and Chamomile blue. In one embodiment, the one or more essential oils present in the product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the product of a material, such as a natural material, that has a high vitamin content.

The advantages of the present invention discussed herein may be applied to any cosmetic product, for example to any emulsion or dispersion. Other cosmetic categories that would be applicable under the present invention include:

shaving preparations, shower gels & shower jellies, moisturisers, skincare & body lotions, sunscreen products, shampoos, conditioners & hair dressings, face masks and lip balms. All are categories of product, which conventionally require packaging, are stored at room temperature and have a long shelf life.

Materials which may be included in the present composition include but are not limited to: Water Phase including—Water, Plant Infusions & Decoctions (including Tea & Coffee), Fruit & Vegetable Juices, Whole Fruit & Vegetables, Vinegar, Beers, Wines & Spirits—typically used in a range of 0.1%-70% for leave-on products and 5%-65% for wash-off products.

Humectants including Honey, Glycerine, Mono Propylene Glycol, 1,2 Propandiol, Agave Nectar, Fruit Syrups, Herbal Syrups, Sugar solutions—typically used in a range of 0.1%-45%

Emulsifiers including—emulsifying solvents such as Triethanolamine & Lactic Acid, emulsifying waxes such as Stearic Acid, Cetearyl Alcohol, Glyceryl Stearate, Cetyl Alcohol/Sodium Laureth Sulfate, Glyceryl Stearate & Polyethylene Glycol 100—typically used in a range of 1.5%-25%

Surfactants (for wash-off products only) including but not limited too—Sodium Lauryl/Laureth Sulfate, Ammonium Lauryl/Laureth Sulfate, Sodium Cocoamphoacetate, Disodium Laureth Sulfosuccinate, Soap, Sodium Stearate, Lauryl Betaine—typically used in a range of 4%-35%

Whole Fruits & Vegetables—Avocado, Banana, Strawberries, Blueberries, typically used in a range of 0.5%-25%.

Fragrance Materials—typically used in a range of 0.1%-5%.

Colorant Materials—typically used in a range of 0.001%-2%

Sunscreens—Octocrylene, Titanium Dioxide, Ethylhexyl Methoxycinnamate—typically used in a range of 3%-25%.

Clays—Kaolin, Talc, Calamine, Rhassoul Mud, Fullers Earth, Bentonite Clays and preparations thereof.—typically used in a range of 0.1%-40%

Salts & Sugars—Sea Salt, Castor Sugar, Granulated Sugar, Brown Sugar, Molasses—typically used in a range of 0.1%-50%

Herbs, Cereals and Beans—Oats, Rice, Cinnamon, Vanilla, Aduki Beans, Seaweeds—typically used in a range of 0.01%-15%

Gelling & Film Forming Agents—Agar Agar, Carrageenan, PVP—typically used in a range of 0.5%-12%

Stabilising Agents—Lactic Acid, Ascorbic Acid, Malic Acid & Fruit Powder—typically used in a range of 0.01%-3%.

Protein Sources—Tofu, Banana, Soya, Soya Lecithin, Eggs—typically used in a range of 1%-30%.

In some aspects, the cosmetic moisturising composition does not comprise wax. In one preferred aspect, the cosmetic moisturising composition does not comprise beeswax.

Process

As discussed herein, the invention provides a process for the production of a cosmetic moisturising composition as described herein;

the process comprising the steps of mixing:

(i) one or more vegetable butters in an amount of from 5 to 35% by weight of the total composition;

(ii) one or more vegetable oils in an amount of from 20 to 50% by weight of the total composition; and (iii) starch in an amount of from 40 to 85% by weight of the total composition;

wherein the cosmetic moisturising composition is free from preservatives, wherein free from preservatives is as defined herein.

As described herein, the solid product may further comprise one or more cosmetically acceptable additives. In one embodiment, the process further comprises the step of combining with the mixture of components (i), (ii) and (iii) one or more cosmetically acceptable additives as defined herein.

The present invention also provides a product obtained or obtainable by a process as defined herein.

Method

In one aspect of the invention, there is provided a method comprising contacting the skin of a user with the cosmetic moisturising composition of the present invention. The product may be self-applied by the user or applied by another individual. In a preferred embodiment, the product is used by the user as a moisturiser.

Example

The invention will now be described with reference to the following non-limiting example.

A cosmetic moisturising composition of the present invention having the following composition was prepared.

| Raw Material | Formula % (wt.) | Batch Size (1000 g) |
| --- | --- | --- |
| Cocoa butter | 12.78 | 127.80 |
| Shea Butter | 7.00 | 70.00 |
| Olive oil | 29.62 | 296.20 |
| Corn Starch | 50.00 | 500.00 |
| Fragrance | 0.60 | 6.00 |
| | 100.00 | 1000.00 |

Method

1. Oils and butters were warmed to 75° C. until all the butter and oils were thoroughly mixed.
2. The molten vegetable butter and vegetable oil blend was cooled to 55° C. and the starches added, followed by blending.
3. The containers were filled with the resulting composition and left to set.

The product was found to be microbiologically stable during storage.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A cosmetic moisturising composition consisting essentially of:
    (i) one or more vegetable butters in an amount of from 5 to 35% by weight of the total composition;
    (ii) one or more vegetable oils in an amount of from 20 to 50% by weight of the total composition;
    (iii) starch in an amount of from 40 to 75% by weight of the total composition, wherein the starch comprises corn starch;
    wherein the cosmetic composition is free from preservatives; and
    (iv) an additional component selected from binders, fillers, opacifiers, perfumes, colours, fragrances and mixtures thereof.

2. A process for production of a cosmetic moisturising composition as defined in claim 1, comprising the step of mixing:
    (i) one or more vegetable butters in an amount of from 5 to 35% by weight of the total composition;
    (ii) one or more vegetable oils in an amount of from 20 to 50% by weight of the total composition; and
    (iii) starch in an amount of from 40 to 85% by weight of the total composition;
    wherein the cosmetic composition is free from preservatives.

3. A cosmetic method comprising contacting skin of a user with a cosmetic composition as defined in claim 1.

4. The cosmetic moisturising composition according to claim 1, wherein the one or more vegetable butters are present in an amount of from 10 to 30% by weight of the total composition.

5. The cosmetic moisturising composition according to claim 1 wherein the one or more vegetable butters are present in an amount of from 15 to 25% by weight of the total composition.

6. The cosmetic moisturising composition according to claim 1, wherein the one or more vegetable butters is a mixture of hard vegetable butter and soft vegetable butter.

7. The cosmetic moisturising composition according to claim 6, wherein
    the hard vegetable butter is selected from Cocoa butter, Illipe butter, Murumuru butter, Kokum butter and mixtures thereof; and
    wherein the soft vegetable butter is selected from Aloe butter, Avocado butter, Cupuacu butter, Macadamia Nut butter, Mango butter, Olive butter, Shea butter, Coconut butter, Pumpkin Seed butter, Peanut butter, Almond butter, Coffee Bean butter, Refined butter, Hemp Seed butter, Mochacchino butter, Pistachio Nut butter, Shealoe butter and mixtures thereof.

8. The cosmetic moisturising composition according to claim 1, wherein the one or more vegetable butters are selected from Cocoa butter, Illipe butter, Murumuru butter, Kokum butter, Aloe butter, Avocado butter, Cupuacu butter, Macadamia Nut butter, Mango butter, Olive butter, Shea butter, Coconut butter, Pumpkin Seed butter, Peanut butter, Almond butter, Coffee Bean butter, Refined butter, Hemp Seed butter, Mochacchino butter, Pistachio Nut butter, Shealoe butter and mixtures thereof.

9. The cosmetic moisturising composition according to claim 1, wherein the one or more vegetable butters is a mixture of Cocoa butter and Shea butter.

10. A cosmetic composition according to claim 1, wherein the one or more vegetable oils are present in an amount of from 20 to 40% by weight of the total composition.

11. A cosmetic composition according to claim 1, wherein the one or more vegetable oils are present in an amount of from 25 to 35% by weight of the total composition.

12. The cosmetic moisturising composition according to claim 1, wherein the one or more vegetable oils are selected from sesame oil, rosehip oil, almond oil, raspberry seed oil, jojoba oil, avocado oil, castor oil, moringa oil, olive oil, grapeseed oil, argan oil, baobab oil, kalahari melon oil, brazil nut oil and mixtures thereof.

13. The cosmetic moisturising composition according to claim 1, wherein the starch is present in an amount of from 40 to 70% by weight of the total composition.

14. The cosmetic moisturising composition according to claim 1, wherein the starch is present in an amount of from 40 to 60% by weight of the total composition.

15. The cosmetic moisturising composition according to claim 1, wherein the additional component is selected from perfumes, colours, fragrances and mixtures thereof.

16. The cosmetic moisturising composition according to claim 1, wherein the composition comprises a fragrance in an amount of from 0.5 to 4% by weight of the total composition.

* * * * *